US00PP11413P

United States Patent [19]

Verwer

[11] Patent Number: Plant 11,413

[45] Date of Patent: Jun. 6, 2000

[54] DAHLIA PLANT NAMED 'KARMA NAOMI'

[75] Inventor: Aad Verwer, DL Lisse, Netherlands

[73] Assignee: Fa. Gebr. Verwer, Lisse, Netherlands

[21] Appl. No.: 09/025,997

[22] Filed: Feb. 19, 1998

[30] Foreign Application Priority Data

Apr. 7, 1997 [NL] Netherlands ..... DHL-75

[51] Int. Cl.[7] ..... A01H 5/00

[52] U.S. Cl. ..... Plt./321

[58] Field of Search ..... Plt./321

[56] References Cited

PUBLICATIONS

GTITM UPOVROM Citation for 'Karma Naomi' as per NL PBRDHL0075; Apr. 7, 1997.

*Primary Examiner*—Howard J. Locker
*Assistant Examiner*—Kent L. Bell
*Attorney, Agent, or Firm*—Christie, Parker & Hale, LLP

[57] ABSTRACT

A dahlia plant variety producing deep mahogany red flowers.

1 Drawing Sheet

BACKGROUND OF THE INVENTION

The present invention relates to a new and distinct variety of *Dahlia hybrida*, known by the varietal denomination 'Karma Naomi'. The female parent of 'Karma Naomi' is an undistributed, unpatented variety known as 'Stratos' and the male parent is an unnamed, undistributed seedling.

SUMMARY OF THE INVENTION

The new variety is a dahlia plant useful for growing outdoors and under glass which produces attractive deep mahogany red flowers on long stems. Among the traits possessed by the new variety which in combination distinguish it from other varieties known to the inventor are its attractive flowers borne on long stems.

Asexual reproduction by cuttings of the new variety in The Netherlands has demonstrated that the combination of characteristics as described herein for 'Karma Naomi' are firmly fixed and are retained through successive generations of asexual reproduction.

COMPARISON WITH PARENTS

The new variety differs from its parents in flower color.

BRIEF DESCRIPTION OF ILLUSTRATION

The accompanying color photographic illustration shows a typical bloom and leaves of the new variety in colors as nearly true as possible with an illustration of this type.

DESCRIPTION OF THE NEW VARIETY

In the following description, color references are to The Royal Horticultural Society Colour Chart, where color values refer to color plate numbers in this chart.

The following observations are of plants described and grown in The Netherlands under outdoor conditions which approximate those generally used in commercial practice. 'Karma Naomi' has not been observed under all possible environmental conditions. The phenotype may vary with variations in environment such as temperature, light intensity, day length and cultural conditions.

Parentage:

*Female parent.*—'Stratos'.

*Male parent.*—unnamed seedling.

Plant:

*Form.*—Upright, spreading.

*Height.*—About 120 cm.

*Branching characteristics.*—Moderately branching.

*Flower stem.*—Length: About 80 to 90 cm. Color: Near 183D.

*Hardiness.*—Plants are winter hardy to 0° C.

*Flowering season.*—July to November in The Netherlands under glass.

*Disease resistance.*—Similar to the species.

*Foliage.*—Single and compound. Quantity: Many. Arrangement and size: Opposite, simple or compound, compound leaves have either three or five leaflets; single leaf about 8.7 cm long, width about 4.9 cm; compound about 21 cm long, about 11 cm wide. Shape of leaf: Ovate, apex and base are acute. Leaf edge: Immature leaves are entire, margin becomes dentate as leaves mature. Texture: Leaf upperside: Smooth. Leaf under side: Smooth. Color: Leaf upperside: Near 146B. Leaf under side: Near 147C. Venation: Pinnate. Stipules: None. Petiole color: Near 183D.

*Sepals.*—Number: 35. Length: 1.6 cm. Width: 1.2 cm. Color: Near 147A. Base: Rounded. Apex: Broadly acute.

*Petiole.*—Longest terminal petioles are about 12 cm; shortest lateral petioles are about 5 cm.

Bud:

*Form.*—Globular.

*Size.*—About 1 cm.

*Opening rate.*—About 15 to 20 days.

*Color of ray florets.*—When sepals first divide near 59A; when ray florets begin to unfurl near 59A.

Flower:

*Inflorescence form.*—Blooms borne singly.

*Bloom form.*—Decorative.

*Bloom size.*—About 13 cm.

*Typical number of blooms harvested per plant per season.*—About 30–40.

*Flowering.*—About 2 to 3 branches are produced, with flowering occurring 35 to 40 days later.

*Color tonality from a distance.*—Deep mahogany red, velvety.

*Lasting quality.*—About 20 to 25 days on plant; about 10 days after cutting.

*Ray florets.*—Length: About 5.2 cm. Width: About 2.2 cm. Shape: Oblong. Apex: Obtuse. Base: Rounded.

*Color.* Ray florets are deep mahogany red with velvety mahogany tonality. Inner ray florets (upper surface and undersurface): Near 66A. Outer ray florets (upper surface and undersurface): Near 64A. Point of ray floret attachment: Near 59A. As bloom ages: Keeps color. Fragrance: None.

*Disc florets.*—Number: About 35. Length: About 1.2 cm. Color: Near 13A. Shape: Cylindric.

Reproductive organs:

*Stamens.*—Many, tubular, near 17A.

*Anthers.*—Small, near 17A.

*Pollen.*—Near 17A.

*Pistils.*—Styles length about 2 mm, color near 1C; stigmas divided, near 15A.

*Character of ovaries.*—1 per pistil.

I claim:

1. A new and distinct dahlia plant of the variety substantially as shown and described.

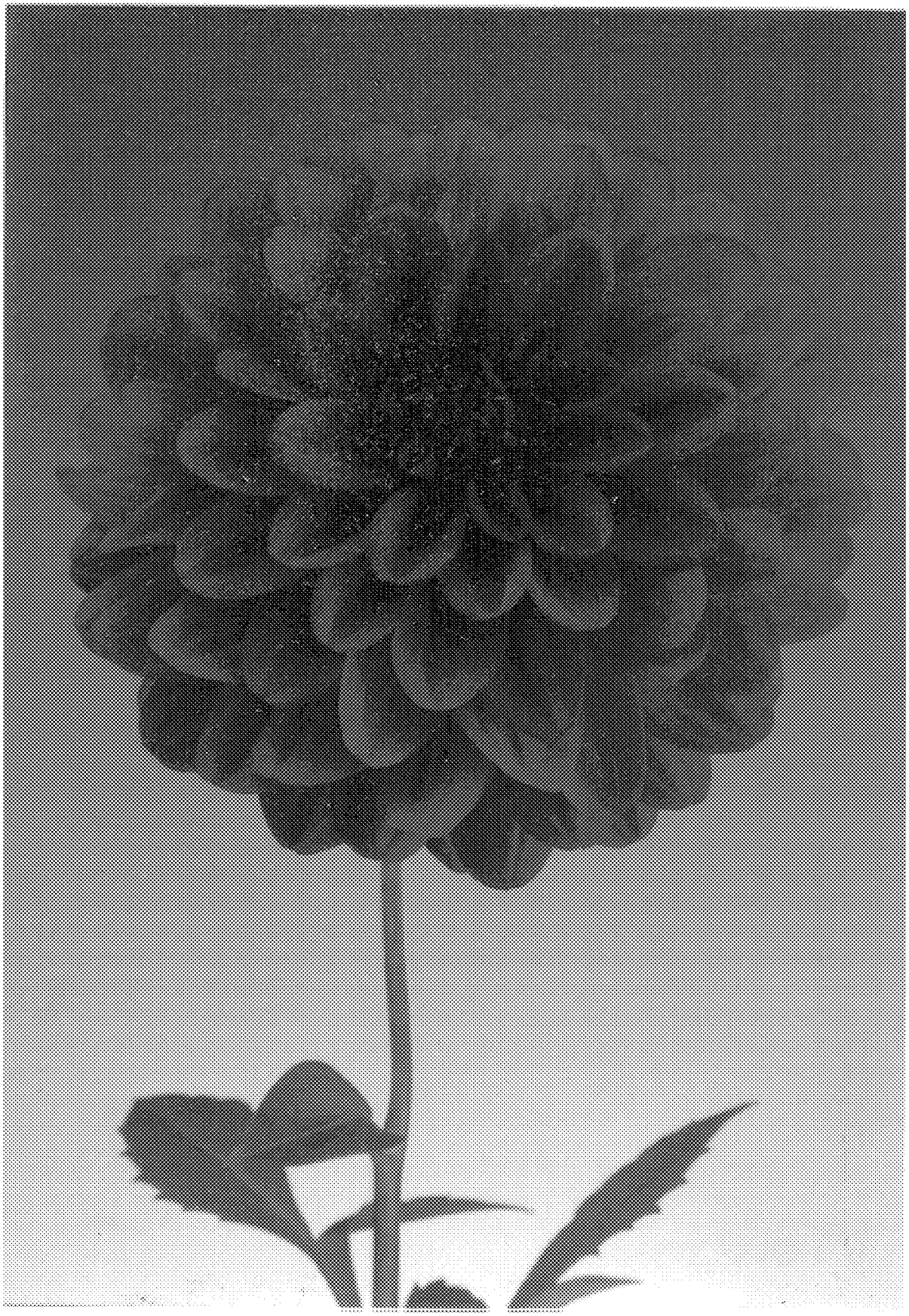

* * * * *